United States Patent
Gray et al.

(10) Patent No.: US 10,492,954 B2
(45) Date of Patent: *Dec. 3, 2019

(54) SECOND PASS FEMTOSECOND LASER FOR INCOMPLETE LASER FULL OR PARTIAL THICKNESS CORNEAL INCISIONS

(71) Applicant: Lensar, Inc., Orlando, FL (US)

(72) Inventors: Gary Gray, Orlando, FL (US); E. Valaski Teuma, Orlando, FL (US)

(73) Assignee: Lensar, Inc., Orlando, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/844,603

(22) Filed: Dec. 17, 2017

(65) Prior Publication Data

US 2018/0104104 A1    Apr. 19, 2018

Related U.S. Application Data

(63) Continuation of application No. 14/444,311, filed on Jul. 28, 2014, now Pat. No. 9,844,465.

(60) Provisional application No. 61/859,737, filed on Jul. 29, 2013.

(51) Int. Cl.
*A61F 9/008* (2006.01)

(52) U.S. Cl.
CPC ........ *A61F 9/00836* (2013.01); *A61F 9/0084* (2013.01); *A61F 9/00827* (2013.01); *A61F 2009/00872* (2013.01); *A61F 2009/00885* (2013.01); *A61F 2009/00897* (2013.01)

(58) Field of Classification Search
CPC ........ A61F 2009/00897; A61F 9/00836; A61F 9/0084; A61F 2009/00872; A61F 2009/00885; A61F 9/00827
See application file for complete search history.

(56) References Cited

U.S. PATENT DOCUMENTS

| | | | |
|---|---|---|---|
| 4,538,608 | A | 9/1985 | L'Esperance |
| 4,764,930 | A | 8/1988 | Bille |
| 4,901,718 | A | 2/1990 | Bille |
| 4,907,586 | A | 3/1990 | Bille |
| 5,246,435 | A | 9/1993 | Bille |
| 5,439,462 | A | 8/1995 | Bille |
| 6,004,314 | A | 12/1999 | Wei |
| 6,322,556 | B1 | 11/2001 | Gwon |
| 7,655,002 | B2 | 2/2010 | Myers |
| 8,262,646 | B2 | 9/2012 | Frey |
| 8,382,745 | B2 | 2/2013 | Naranjo-Tackman |
| 8,394,084 | B2 | 3/2013 | Palankar et al. |

(Continued)

OTHER PUBLICATIONS

Dec. 13, 2017, Chinese Patent Office, Translation of Office Action in Appl. No. 201410366682.8.

(Continued)

*Primary Examiner* — Scott Luan
(74) *Attorney, Agent, or Firm* — Glen P. Belvis; Belvis Law, LLC.

(57) ABSTRACT

A method for forming an incision in an eye, the method including performing a first pass of a first laser beam along a path within an eye, wherein after completion of the first pass there exists a residual uncut layer at an anterior surface of a cornea of the eye. The method further including performing a second pass of a second laser beam only along a portion of the path that contains the residual uncut layer, wherein after completion of the second pass, the residual uncut layer is transformed into a full complete through surface incision.

12 Claims, 3 Drawing Sheets

First Pass Beam Path

(56) References Cited

U.S. PATENT DOCUMENTS

| | | |
|---|---|---|
| 8,403,921 B2 | 3/2013 | Palankar et al. |
| 8,425,497 B2 | 4/2013 | Blumenkranz et al. |
| 8,465,478 B2 | 6/2013 | Frey |
| 8,480,659 B2 | 7/2013 | Frey |
| 8,500,723 B2 | 8/2013 | Frey |
| 8,617,146 B2 | 12/2013 | Frey |
| 8,758,332 B2 | 6/2014 | Frey |
| 8,801,186 B2 | 8/2014 | Frey |
| 9,180,051 B2 | 11/2015 | Frey |
| 9,375,349 B2 | 6/2016 | Frey |
| 9,545,338 B2 | 1/2017 | Frey |
| 2007/0173794 A1 | 7/2007 | Frey |
| 2008/0287928 A1 | 11/2008 | Arnoldussen |
| 2010/0004641 A1 | 1/2010 | Frey |

OTHER PUBLICATIONS

Dec. 13, 2017, Chinese Patent Office, Office Action in Appl. No. 201410366682.9.

Dec. 13, 2017, Chinese Patent Office, Translation of Office Action in Appl. No. 20141036682.8.

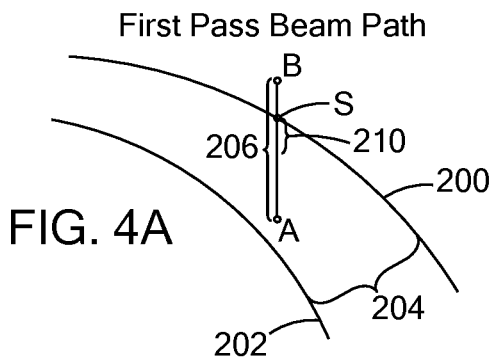
FIG. 4A — First Pass Beam Path
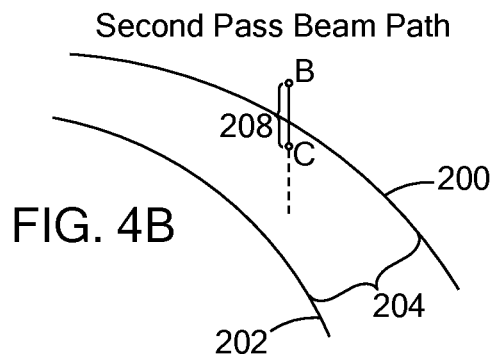
FIG. 4B — Second Pass Beam Path
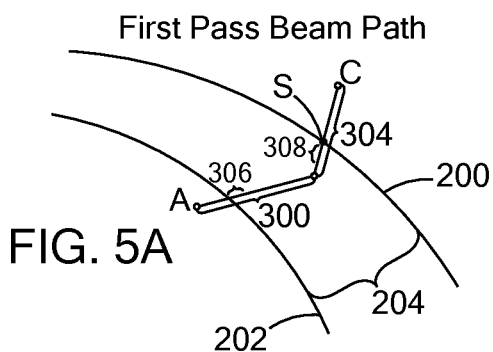
FIG. 5A — First Pass Beam Path
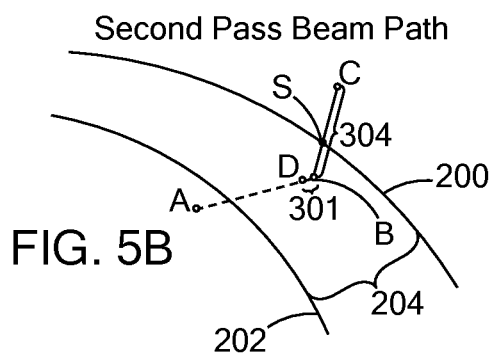
FIG. 5B — Second Pass Beam Path
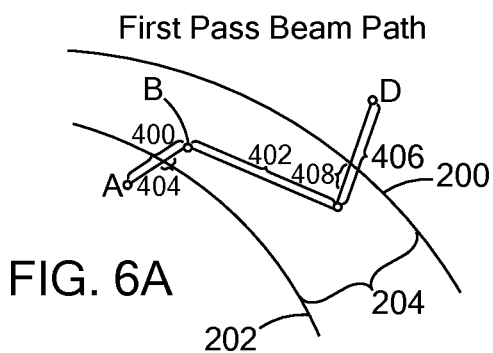
FIG. 6A — First Pass Beam Path
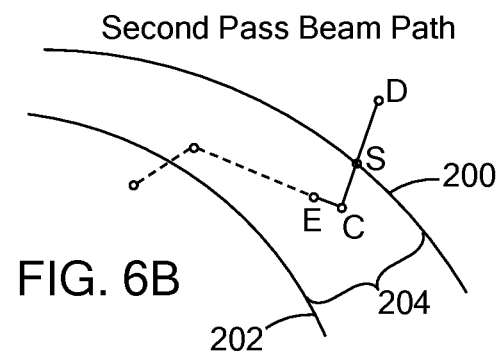
FIG. 6B — Second Pass Beam Path

SECOND PASS FEMTOSECOND LASER FOR INCOMPLETE LASER FULL OR PARTIAL THICKNESS CORNEAL INCISIONS

This application is a continuation of U.S. patent application Ser. No. 14/444,311 filed Jul. 28, 2014, which claims pursuant to 35 U.S.C. § 119 (e) the benefit of priority of U.S. provisional application Ser. No. 61/859,737, filed Jul. 29, 2013, the entire disclosure of each of which is-incorporated herein by reference.

BACKGROUND OF THE INVENTION

Field of the Invention

The present invention relates to methods and systems for improving surgical procedures for improving incomplete full or partial thickness corneal incisions.

Discussion of Related Art

Presently, there are a number of surgical methods for correcting maladies of the eye that involve forming an incision in the cornea of the eye. For example, it is known to surgically correct astigmatism by forming limbal relaxing incisions (LRIs) in the eye, wherein such LRIs are generally paired arcuate incisions/cuts formed in the cornea of the eye. In the past, such incisions were formed manually with a fixed or variable depth blade.

Recently, the practice of making the incisions manually with the above mentioned fixed or variable depth blade is starting to be supplanted by incisions made with a femtosecond laser (Maxine Lipner, EyeWorld, "What's Ahead, Femtosecond technology changing the cataract landscape", 2011 Mar. 24 8:45:27). Such a laser makes incisions by focusing ultrashort laser pulses to a very fine focus, causing a plasma mediated photodisruption of the tissue at the point of focus. An incision is generated by placing a contiguous series of such pulses in a pattern that results in the formation of the desired incision. To make a corneal incision, the point of focus of a femtosecond laser is scanned across a planar or curved surface within the volume of the target tissue to form the incision. The beam intensity at the focus is chosen to substantially exceed the laser induced optical breakdown threshold of the tissue. As each pulse is delivered, a plasma-mediated photo-disruption occurs, vaporizing a miniscule volume of tissue at or near the point of focus. A cavitation bubble subsequently forms near the point of focus which helps cleave the damaged region to form the incision. Using a scanning laser guidance system, laser pulses are placed contiguously in three dimensions across the desired planar or curved surfaces to form the overall incision. The combined effect of the pattern of pulses is to cleave the tissue at the targeted plane. Arbitrarily complex incisions patterns can be generated with such lasers. The femtosecond lasers are believed to make incisions of a more accurate and consistent depth and of a curvature that more accurately matches the desired arcuate form of the incision.

There can be circumstances where the above mentioned femtosecond laser generates a low numerical aperture (NA) (or slow F-Theta lens) laser beam and is paired with a liquid patient interface. A comparison between a high numerical aperture laser beam 100 that passes through a liquid patient interface 102 and a low numerical aperture laser beam 104 that pass through a liquid patient interface 102 is shown in FIGS. 1A and 1B. As shown in FIG. 1A, a high numerical aperture laser beam 100 passes through a liquid patient interface 102, resulting in a focused high numerical aperture laser beam 106. The focused high numerical aperture laser beam 106 is directed into a portion 108 of the anterior corneal surface of the cornea of the eye and the beam 106 reaches the rear portion 110 of the portion 108.

As shown in FIG. 1B, a low numerical aperture laser beam 104 passes through a liquid patient interface 102, resulting in a focused low numerical aperture laser beam 112. The focused high numerical aperture laser beam 112 is directed into a portion of the anterior corneal surface 108 of the cornea of the eye and the beam 112, the corneal entry incision leaves an unintended residual thin but uncut layer 114 at the anterior corneal surface, such as at the Bowman's membrane of the cornea which has the stiffest collagen fibers and at the posterior corneal surface, such as Descemet's membrane which is relatively softer. The formation of the unintended uncut layer 114 is due to the fact that there is a difference at the interface between the optical breakdown thresholds of the epithelium layer of the cornea and the Bowman's membrane of the cornea at the anterior corneal surface of the cornea of the eye. Similarly, an uncut layer at the posterior corneal surface is formed due to the optical breakdown thresholds of the endothelium layer of the cornea and the Descemet's membrane of the cornea at the posterior corneal surface of the cornea of the eye. An example of such an unintended uncut layer is shown in FIGS. 2A-B and 3A-B. Note that the unintended uncut layer can be generated in a variety of incisions. For example, uncut layers 116, 118 of FIGS. 2A-B and 3A-B can be generated in a so called Full Thickness corneal Incision (FTI), which is an intended incision from posterior to anterior surface of the cornea as would be the case for Clear Corneal Incisions (CCIs), paracentesis incisions or Penetrating Keratoplasty (PKP) or other through surface modalities. As another example, the uncut layer can be generated in a so called Partial Thickness Incision (PTI), which intentionally starts within the stroma and progresses through the anterior surface of the eye as would be the case for Limbal Relaxing Incision (LRI) and Astigmatic Keratotomy (AK) or other partial thickness modalities. In either example, the presence of the uncut layer results in an incomplete FTI or PTI incision being formed. Note that in either the FTI or PTI incision, the thickness of the residual uncut layer can vary from approximately 10 μm to approximately 30 μm, as a function of the numerical aperture and the output energy of the laser beam.

One shortcoming of the incomplete full or partial thickness corneal incisions of FIGS. 2A-B and 3 A-B is that it can be relatively difficult to locate and open the wound due to the strength of the residual thin layers 116, 118 left uncut. For human eyes, the residual uncut layers encompass the Bowman's membrane, for partial thickness corneal incisions, and, Bowman's and Descemet's membranes, for full thickness corneal incision. Bowman's and Descemet's membranes are the regions of the eye structure with the stiffest collagen fibers.

SUMMARY

One aspect of the invention regards a method for forming an incision in an eye, the method including performing a first pass of a first laser beam along a path within an eye, wherein after completion of the first pass there exists a residual uncut layer at an anterior surface of a cornea of the eye. The method further including performing a second pass of a second laser beam only along a portion of the path that contains the residual uncut layer, wherein after completion of the second pass, the residual uncut layer is transformed into a full complete through surface incision.

One or more aspects of the present invention provides for the generation of a full through surface corneal incision in a dependable manner.

One of ordinary skill in the art will recognize, based on the teachings set forth in these specifications and drawings, that there are various embodiments and implementations of these teachings to practice the present invention. Accordingly, the embodiments in this summary are not meant to limit these teachings in any way.

BRIEF DESCRIPTION OF THE DRAWINGS

FIG. 4A schematically shows a first partial incision formed by a first possible surgical process in accordance with the present invention;

FIG. 4B schematically shows a first full incision based on the first partial incision of FIG. 4A formed by a first possible surgical process in accordance with the present invention;

FIG. 5A schematically shows an embodiment of first pass of a first femtosecond laser beam in accordance with a second possible surgical process in accordance with the present invention;

FIG. 5B schematically shows an embodiment of second pass of a second femtosecond laser beam in accordance with a second possible surgical process in accordance with the present invention;

FIG. 6A schematically shows an embodiment of first pass of a first femtosecond laser beam in accordance with a third possible surgical process in accordance with the present invention;

FIG. 6B schematically shows an embodiment of second pass of a second femtosecond laser beam in accordance with a third possible surgical process in accordance with the present invention.

DESCRIPTION OF THE DRAWINGS AND THE PREFERRED EMBODIMENTS

Figure 1A:
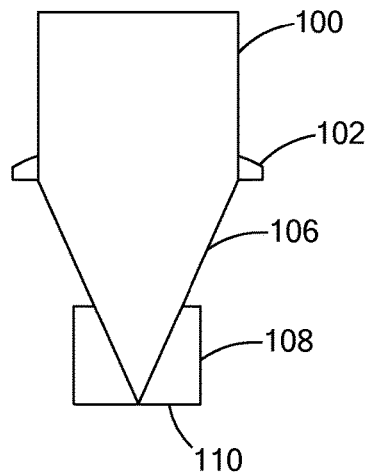
FIG. 1A schematically shows a laser beam with a high numerical aperture.
Figure 1B:
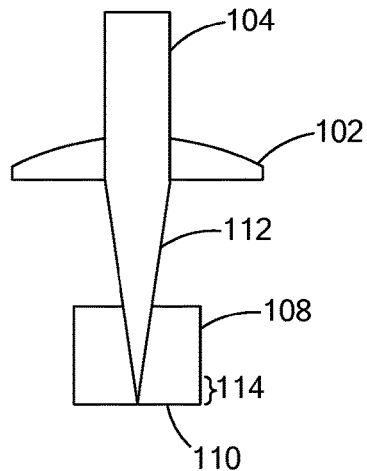
FIG. 1B schematically shows a laser beam with a low numerical aperture.

In general, the present invention relates to a method of generating a complete through surface incision of a portion of the eye, such as a complete incision of a full thickness or partial thickness of the cornea of the eye. An example of a possible partial thickness corneal incision (PTI) of the anterior corneal surface of an eye is shown in FIGS. 4 A-B. Examples of full thickness corneal incisions (FTI) are shown in FIGS. 5-6.

In FIG. 4A, an anterior surface 200 and a posterior surface 202 of a cornea 204 of an eye are shown. A first pass of a first femtosecond laser beam is performed in its entirety at a low energy above the photo-disruption threshold. The first laser beam has an energy in a range of 3 µJ-5 µJ and is a low numerical aperture laser beam that passes through a liquid patient interface 201, wherein a low numerical aperture laser beam is used so that the laser focal point will be far enough to reach the lens posterior region and effectively fragment cataractous materials within the eye. In particular, the first pass of the first laser beam begins at a position A within the cornea 204 and moves linearly toward a position B located past the anterior surface 200 and in a chamber filled with a balanced salt solution (BSS). As shown in FIGS. 4A-B, the first pass is along a linear path, wherein a first full cut 206 is formed. Along the path of the first full cut 206, just below the anterior surface of the cornea, an uncut region 210 can remain. As shown in FIG. 4B, subsequent to the first pass, a second pass 208 of a second femtosecond laser beam that is a low numerical aperture laser beam is performed at an energy, such as 6 µJ-14 µJ, which is greater in value than the energy of the first femtosecond laser beam. The second pass 208 is performed along a portion of the same linear path as the first pass that is near the anterior surface 200 of the cornea 204. In particular, the second pass 208 begins at the point C prior to the uncut layer 210 and ends at position B. Point C is at a pre-programmed distance 209 below the corneal surface S (200), typically 100-300 µm. In other words, the second pass 208 includes the uncut layer 210 and extends to the end of the overcut at point B.

Figure 7:
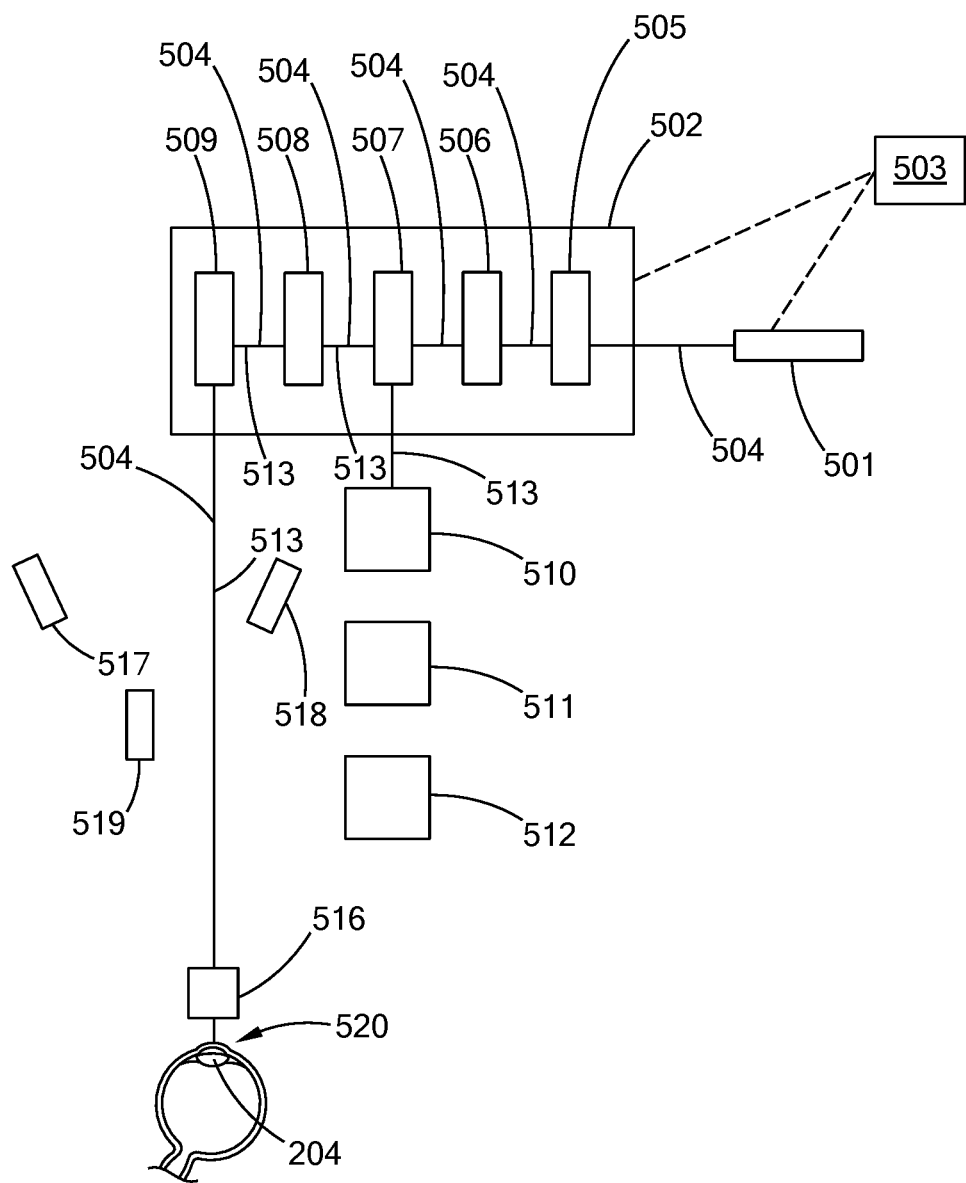
FIG. 7 shows an embodiment of a surgical device to form the incisions of FIGS. 4-6 in accordance with the present invention.

Note that prior to executing any incisions, the laser system of FIG. 7 uses built in biometry scanning to automatically map the anterior and/or posterior cornea surfaces at the incision site and automatically determines beam path for both the first and second passes. In the present case, such automatic mapping and determining would identify the first pass path A→B. With the corneal anterior surface S also being identified, the system traces back along the path, starting at the surface S (200), for a predetermined distance, typically 100-300 µm to position the second pass start point C. After completion of the first pass, a one-plane partial thickness incision is formed, wherein the term "one-plane" regards the fact that the resultant path from the first pass is contained within a single plane. The term "partial thickness" regards the fact that the start point A is intentionally within the body of the cornea.

In FIG. 5A, a first pass of a first femtosecond laser beam is performed in its entirety at a low energy above the photo-disruption threshold. The first laser beam is a low numerical aperture laser beam that passes through a liquid patient interface 201. In particular, the first pass begins at a position A in the aqueous humor of the eye, moves linearly toward a position B located in the interior of the cornea 204, and then changes direction and moves linearly to position C past the anterior surface 200 and in a chamber filled with a balanced salt solution. The first pass is along an angled path, wherein two linear cuts 300 and 304 are formed. When attempting to cut across the junction between dissimilar media (e.g. cornea to BSS or stoma to Bowman's membrane), the difference in optical breakdown threshold will result in small uncut regions being formed. Just above the posterior corneal surface, in segment 300, an uncut layer 306 remains. Just below the anterior corneal surface, in the last full cut segment 304, a second uncut layer 308 remains.

As shown in FIG. 5B, subsequent to the first pass, a second pass of a second femtosecond laser beam that is a low numerical aperture laser beam is performed. Note that the energies of the first and second passes of the first and second laser beams are similar to the energies of the first and second laser beams of FIGS. 4A-B. The second pass is performed along a portion of the same linear path as the first pass that is near the anterior surface 200 of the cornea 204. In particular, the second pass begins at the point D prior to the region of uncut cornea 308 and ends at position C so as to define portion 301. In other words, the second pass includes the uncut layer 308.

Note that prior to executing any incisions, the laser system of FIG. 7 uses built in biometry scanning to automatically map the anterior and/or posterior cornea surfaces at the incision site and automatically determines beam path for both the first and second passes. In the present case, such automatic mapping and determining would identify the first pass path A→B→C. With the corneal anterior surface S (200) also being identified, the system traces back along the path S→B→A, starting at the surface S, for a predetermined distance, typically 100-300 µm, to position the second pass start point D. The second pass path is also defined as D→B→C. Should the programmed length of the second pass be such that D lies on the segment S→B, then the second pass will be simply defined by the linear path D→S.

Note that there is no need for a second pass at the uncut layer 306, since the Descement membrane's stiffness is such that the thin uncut layer of the uncut layer 306 will be broken naturally from structural weakness and the residual heat emanating from the laser beam's upward displacement in the aqueous humor of the eye.

After completion of both passes, a two-plane full thickness incision is formed, wherein the term "two-plane" regards the fact that the resultant incision forms two planes. The term "full thickness" regards the fact that the resultant incision intentionally cuts from the posterior to anterior surface of the cornea.

In FIG. 6A, a first pass of a first femtosecond laser beam is performed in its entirety at a low energy above the photo-disruption threshold. The laser beam is a low numerical aperture laser beam that passes through a liquid patient interface 201. In particular, the first pass begins at a position A in the aqueous humor of the eye, moves linearly toward a position B located in the interior of the cornea 204, and then changes direction and moves linearly to position C. Next, the laser beam changes direction and moves linearly past the anterior surface 200 to a position D in a chamber filled with a balanced salt solution. The first pass is along a zigzag angled path, wherein linear full cuts 400, 402 and 406 are formed. Just above the posterior corneal surface, in segment 400, an uncut layer 404 remains. Just below the anterior corneal surface, in the last full cut segment 406, a second uncut layer 408 remains.

As shown in FIG. 6B, subsequent to the first pass, a second pass of a second femtosecond laser beam that is a low numerical aperture laser beam is performed. Note that the energies of the first and second passes of the first and second laser beams are similar to the energies of the first and second laser beams of FIGS. 4A-B. The second pass is performed along a portion of the same linear path as the first pass that is near the anterior surface 200 of the cornea 204. In particular, the second pass begins at the point E prior to the region of uncut cornea 408 and ends at position D. In other words, the second pass includes the uncut layer 408. Note that prior to executing any incisions the laser system of FIG. 7 uses built in biometry scanning to automatically map the anterior and/or posterior cornea surfaces at the incision site and automatically determines the second pass path. In the present case, such automatic mapping and determining would identify the first pass path A→B→C→D. With the corneal anterior surface S being identified, the system traces back along the first pass path, starting at the surface S, for a predetermined distance, typically 100-300 µm to position the second pass start point E. The system then performs a second pass along the path E→C→D. Note that if the length S→C is greater than the second pass length then the second pass will be performed along a single linear path E→D.

Note that there is no need for a second pass at the uncut layer 404, since the Descement membrane's stiffness is such that the thin uncut layer of the uncut layer 404 will be broken naturally from structural weakness and the residual heat emanating from the upstream laser beam in the aqueous humor of the eye.

After completion of both passes, a three-plane full thickness incision is formed, wherein the term "three-plane" regards the fact that the resultant incision forms three planes. The term "full thickness" regards the fact that the resultant incision intentionally cuts from the posterior to anterior surface of the cornea.

Note that there are several principles involved regarding the use of a second pass on the incomplete cuts at the anterior surface of the cornea for the incisions shown in FIGS. 4A-B, 5A-B and 6A-B. First, the second pass results in increased visibility of the incision entrance for the surgeon. Second, the stiffness of the Bowman's membrane is much greater than that of the Descement's membrane and so structural weakness of the Bowman's membrane and residual heat from the air bubbles produced by photodisruption in the balanced salt solution will not be sufficient in themselves to break the uncut layer at the anterior surface of the cornea. Thus, a second pass of the laser beam is necessary break the uncut layer. On a related point, the present two-pass technique avoids the use of just a single pass of a laser beam to form a full cut at the anterior surface of the cornea. Most nerves reside between the endothelial cells and the Bowman's membrane and so a single pass laser technique could induce unwarranted pain to the patient due to the aggravation of the nerves by the laser. In contrast, the presently described two pass technique results in the further softening of the residual uncut layers and so helps to ease the opening of the wound.

In order to form the first and second pass patterns of FIGS. 4-6, a laser system is provided as shown in FIG. 7 and as described in U.S. patent application Ser. No. 12/831,783, the entire contents of which are incorporated herein by reference. In particular, the laser system includes a treatment laser 501 which should provide a beam 504. The beam should be of a short pulse width, together with the energy and beam size, to produce photodisruption. Thus, as used herein, the term laser shot or shot refers to a laser beam pulse delivered to a location that results in photodisruption. As used herein, the term photodisruption essentially refers to the conversion of matter to a gas by the laser, with accompanying shock wave and cavitation bubble. The term photodisruption has also been generally referred to as Laser Induced Optical Breakdown (LIOB). In particular, wavelengths of about 300 nm to 2500 nm may be employed. Pulse widths from about 1 femtosecond to 100 picoseconds may be employed. Energies from about a 1 nanojoule to 1 millijoule may be employed. The pulse rate (also referred to as pulse repetition frequency (PRF) and pulses per second measured in Hertz) may be from about 1 KHz to several GHz. Generally, lower pulse rates correspond to higher pulse energy in commercial laser devices. A wide variety of laser types may be used to cause photodisruption of ocular tissues, dependent upon pulse width and energy density. Thus, examples of such lasers are disclosed in U.S. Patent Application Publication No. 2007/084694 A2 and WO 2007/084627A2, the entire contents of each of which are incorporated herein by reference. These and other similar lasers may be used as therapeutic lasers. For procedures on the cornea the same type of therapeutic laser as described herein may be used, with the energy and focal point being selected to perform the desired procedure.

In general, the optics 502 for delivering the laser beam 504 to the structures of the eye should be capable of providing a series of shots to the natural lens in a precise and predetermined pattern in the x, y and z dimension. The z dimension as used herein refers to that dimension which has an axis that corresponds to, or is essentially parallel with the anterior to posterior (AP) axis of the eye. The optics should also provide a predetermined beam spot size to cause photodisruption with the laser energy reaching the structure of the eye intended to be cut.

In general, the control system 503 for delivering the laser beam 504 may be any computer, controller, and/or software hardware combination that is capable of selecting and controlling x-y-z scanning parameters and laser firing. These components may typically be associated at least in part with circuit boards that interface to the x-y scanner, the z focusing device and/or the laser. The control system may also, but does not necessarily, have the further capabilities of controlling the other components of the system, as well as, maintaining data, obtaining data and performing calculations. Thus, the control system may contain the programs that direct the laser through one or more laser shot patterns. Similarly, the control system may be capable of processing data from the slit scanned laser and/or from a separate controller for the slit scanned laser system.

The laser optics 502 for delivering the laser beam 504 includes a beam expander telescope 505, a z focus mechanism 506, a beam combiner 507, an x-y scanner 508, and focusing optics 509. There is further provided relay optics 510, camera optics 511, which include a zoom, and a first ccd camera 512.

Optical images of the eye 514 and in particular optical images of the natural lens of the eye 520 are conveyed along a path 513. This path 513 follows the same path as the laser beam 504 from the natural lens through the laser patient interface 516, the focusing optics 509, the x-y scanner 508 and the beam combiner 507. There is further provided a laser patient interface 516, a structured light source 517 and a structured light camera 518, including a lens. Examples of patient interface and related apparatus that are useful with the present system are provided in regular and provisional U.S. patent application Ser. No. 12/509,021 and Ser. No. 61/228,457, wherein each was filed on the same day as the present application and wherein the entire disclosures of each of which are incorporated herein by reference.

The structured light source 517 may be a slit illumination having focusing and structured light projection optics, such as a Schafter+Kirchhoff Laser Macro Line Generator Model 13LTM+90CM, (Type 13LTM-250S-41+90CM-M60-780-5-Y03-C-6) or a StockerYale Model SNF-501L-660-20-5, which is also referred to as a slit scanned laser. In this embodiment the structured illumination source 517 also includes slit scanning means 519. The operation of using a scanned slit illumination is described in described in U.S. patent application Ser. No. 12/831,783.

Figure 2A:
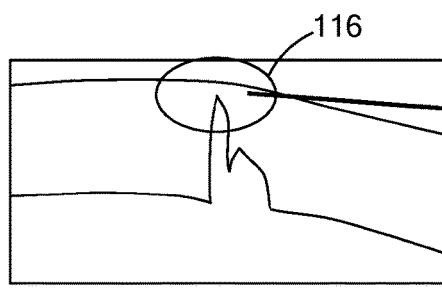
FIG. 2A is a photograph of a residual thin uncut layer of an intended full thickness 1-plane corneal incision.
Figure 2B:
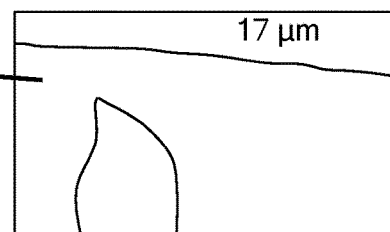
FIG. 2B is an enlarged portion of the photograph of FIG. 2A.
Figure 3A:
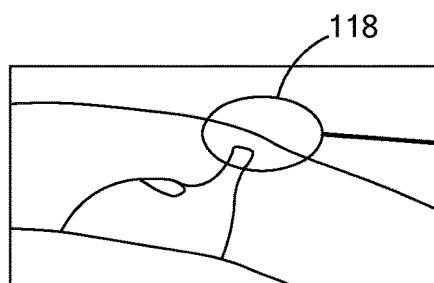
FIG. 3A is a photograph of a residual thin uncut layer of an intended full thickness 3-plane corneal incision.
Figure 3B:
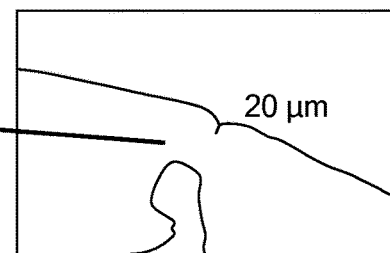
FIG. 3B is an enlarged portion of the photograph of FIG. 3A.

The images from the camera 518 may be conveyed to the controller 503 for processing and further use in the operation of the system. They may also be sent to a separate processor and/or controller, which in turn communicates with the controller 503. The structured light source 517, the camera 518 and the slit scanning means 519 include a means for determining the position and apex of the lens in relation to the laser system. Based at least on part from the determined position and apex of the lens, the scanning of the laser beam 504 upon the eye 520 can be controlled by controller 503. For example, to make a corneal incision, a point of focus of a laser, such as a femtosecond laser, generates a low numerical aperture beam that passes through a liquid patient interface 201 that adjoins the eye and is scanned during a first pass across a planar or curved surface within the volume of the target tissue to form the incision. The beam is a low numerical aperture beam and has an intensity at focus is chosen to be at a low energy that just exceeds the laser induced optical breakdown threshold of the tissue. As each pulse is delivered, a plasma-mediated photo-disruption occurs, vaporizing a miniscule volume of tissue at or near the point of focus. A cavitation bubble subsequently forms near the point of focus which helps cleave the damaged region to form the incision. Using a scanning laser guidance system as shown in FIG. 6, laser pulses are placed contiguously in three dimensions across the desired planar or curved surfaces to form the overall incision. During the first pass of the laser beam, a partial cut will result in the manner discussed with respect to FIGS. 2A-B. In this situation, a second pass of a laser beam is automatically performed shortly after completion of the first pass wherein scanning of a second low numerical aperture laser beam that passes through the liquid patient interface is performed at a higher energy and scanning speed when compared with the first pass. The second pass involves having the laser beam follow a portion of the same path as followed by the laser beam of the first pass near the anterior surface of the cornea. At least in the case of making an incision into an anterior portion of the cornea, the laser parameters, including energy and scanning speed, are optimized to cut through the denser cells without compromising effectiveness within the stroma. For example, during the first pass, the XY spacing between shots ranges from 4 to 8 µm, the Z spacing of the shots ranges from 4 to 5 m, the energy ranges from 3 to 5 J and the pulse repetition frequency is approximately 80 kHz. During the second pass, the XY spacing between shots ranges from 6 to 10 µm, the Z spacing of the shots ranges from 4 to 8 µm, the energy ranges from 6 to 14 µJ and the pulse repetition frequency is approximately 80 kHz. After scanning of the second pass, the partial cut near the anterior surface of the cornea has evolved into a full cut. Note that in the case of making an incision at the anterior surface portion of the cornea, the incision extends only minimally into the stroma. Note that the above mentioned two pass process can be applied to form the incisions shown in FIGS. 4-6.

From the foregoing description, one skilled in the art can readily ascertain the essential characteristics of this invention, and without departing from the spirit and scope thereof, can make various changes and/or modifications of the invention to adapt it to various usages and conditions.

We claim:

1. A method for forming an incision in an eye, the method comprising:

performing a first pass of a first laser beam along a first portion of a path within the cornea of an eye, the pass starting from a point within the cornea and moving toward the anterior surface of the cornea; thereby forming an incision within the cornea; wherein after completion of the first pass there exists a residual uncut layer at the anterior surface of the cornea, wherein the residual layer includes Bowman's membrane;

performing a second pass of a second laser beam along a second portion of the path; the first and second portions of the path at least partially overlapping; wherein the second portion of the path contains the residual uncut layer, wherein after completion of said second pass, the residual uncut layer is transformed into a full complete through surface incision.

2. The method of claim 1, wherein said first laser beam has a low numerical aperture and passes through a liquid-filled patient interface before penetrating said eye, and wherein said residual uncut layer is the result of said first laser beam passing through said liquid-filled patient interface.

3. The method of claim 1, wherein said path is formed in a cornea of an eye.

4. The method of claim 1, wherein said first laser beam has a different energy than said second laser beam.

5. The method of claim 1, wherein said first laser beam is at a first energy of 3 µJ to 5 µJ, wherein the first energy exceeds a photodisruption threshold and said second laser beam is at a second energy that is higher than the first energy.

6. The method of claim 1, wherein said first laser beam is scanned along said path at a different rate than said second laser beam is scanned along said portion of said path that contains said partial thickness incision.

7. The method of claim 1, wherein said path is a linear path and said portion of said path that contains said residual uncut layer is linear.

8. The method of claim 1, wherein said path is an angular path and said portion of said path that contains said residual uncut layer is linear.

9. The method of claim 1, wherein said path is an angular path and said portion of said path that contains said residual uncut layer is angular.

10. The method of claim 1, wherein said first laser beam has a pulse width that is less than one femtosecond and said second laser beam has a pulse width that is less than one femtosecond.

11. The method of claim 1, wherein after completion of said second pass, a full thickness corneal incision is formed.

12. The method of claim 1, wherein after completion of said second pass, a partial thickness corneal incision is formed.

* * * * *